United States Patent [19]

Terada et al.

[11] Patent Number: 4,751,930
[45] Date of Patent: Jun. 21, 1988

[54] BLOOD PRESSURE MEASURING SYSTEM

[75] Inventors: Haruhiro Terada, Yahata; Kouichi Ishino; Nobuo Iwai, both of Hikone, all of Japan

[73] Assignee: Matsushita Electric Works, Ltd., Osaka, Japan

[21] Appl. No.: 878,081

[22] Filed: Jun. 24, 1986

[30] Foreign Application Priority Data

Jul. 12, 1985 [JP] Japan ............................ 60-154789

[51] Int. Cl.$^4$ ............................................. A61B 5/02
[52] U.S. Cl. ............................................... 128/681
[58] Field of Search ............................ 128/680–683, 128/687–690; 364/415, 417

[56] References Cited

U.S. PATENT DOCUMENTS

| | | | |
|---|---|---|---|
| 4,105,021 | 8/1978 | Williams et al. | 128/683 |
| 4,106,498 | 8/1978 | Haney | 128/681 |
| 4,140,110 | 2/1979 | Jansen et al. | 128/681 |
| 4,167,181 | 9/1979 | Lee | 128/682 |
| 4,177,801 | 11/1979 | Grangirard et al. | 128/681 |
| 4,313,445 | 2/1982 | Georgi | 128/680 |
| 4,326,537 | 4/1982 | Croslin | 128/687 |
| 4,427,013 | 1/1984 | Nunn et al. | 128/681 |
| 4,442,845 | 4/1984 | Stephens | 128/687 |

Primary Examiner—Francis J. Jaworski
Attorney, Agent, or Firm—Armstrong, Nikaido, Marmelstein & Kubovcik

[57] ABSTRACT

An improved blood pressure measuring system based on oscillometric methods utilizes a pressure transducer which provides a varying cuff pressure for occluding the artery of a test subject. The cuff pressure is sampled at a suitable sampling rate to provide a consistent waveform including arterial or blood pressure pulses appearing in sequence during the period of decreasing the occluding pressure. Each blood pressure pulse superimposed upon the cuff pressure is extracted as a pulsating quantity for analyzing the characteristic behavior of such arterial pulse train in order to determine required blood pressure measurements. The pulsating quantity is defined to be an integral of each pulse which value is much larger than the height of the pulse and accordingly, represents an index more readily discernable from possible artifacts having a level in the vicinity of the height level of the pulse.

5 Claims, 12 Drawing Sheets

BLOOD PRESSURE MEASURING SYSTEM

BACKGROUND OF THE INVENTION

1. Field of the Invention

The present invention is directed generally to a blood pressure measuring system, and more particularly to an improved blood pressure measuring system utilizing oscillometric methods for determination of the blood pressure measurements of a test subject.

2. Description of the Prior Art

There have been proposed in the art a number of blood pressure measuring systems based upon the oscillometric methods, for example, as shown in U.S. Pat. Nos. 4,263,918 and 4,407,297. The prior systems relying upon the oscillometric methods handle the fluctuating quantity representative of each blood pressure pulse appearing within an artery of the subject under a changing external pressure of occluding the artery for the purpose of analyzing the oscillometric pulse train and determining systolic and diastolic pressures. The practical implementation of the system is to employ a pressure transducer which delivers at a suitable sampling rate the cuff pressure data including the occluding pressure plus the blood pressure pulse superimposed thereon. In the above prior system, the blood pressure pulse is extracted from the cuff pressure data in the form of a pulse height or peak value as representing the fluctuating or pulsating quantity.

But unfortunately, the blood pressure pulse superimposed on the occluding pressures is known to be normally as small as 5 mmHg in height, which not only makes the extraction technique thereof difficult but also makes the extracted value rather incompetent against possible artifacts which frequently accompany an even slight movement of the subject during the measurement cycle or unavoidable artifacts generated within the body of the subject. Accordingly, the prior systems recognizing the blood pressure pulses by their pulse height are susceptible to the artifacts and likely to result in false or erroneous calibration, which should be eliminated for effectuating accurate and easy blood pressure measurements.

SUMMARY OF THE INVENTION

The present invention eliminates the above problem and has its primary object of presenting a blood pressure measuring system which can well discern the blood pressure pulses from the artifacts and is capable of giving more accurate and reliable measurement results. The blood pressure measuring system in accordance with the present invention comprises an occluding cuff for applying a varying occluding pressure to the artery of a test subject and bleeding means for allowing the occluding pressure to gradually decrease. Pressure transducer means communicates with the occluding cuff to produce at a suitable sampling rate instantaneous cuff pressure data. The sampled cuff pressure data is processed to extract a pulsating quantity representative of each of arterial blood pressure pulses occurring in sequence during the course of bleeding down the occluding pressure as well as to extract a static cuff pressure at the onset of each blood pressure pulse superimposed thereupon. The pulsating quantity thus extracted is then processed for determination of the blood pressure measurements. The characteristic feature of the present invention resides in that the pulsating quantity is defined in terms of an integral of the blood pressure pulse above an offset value corresponding to the static pressure on which the pulse is superimposed. With this methodology of treating the pulsating quantity in terms of an integral of the blood pressure pulse, it is readily possible to discern the blood pressure pulse from possible artifacts within the body of the subject for assuring accurate analysis of the blood pressure pulses, even in the case that such artifacts are of the same level as the pulse height of the blood pressure pulse. In fact, the pulse height of the blood pressure pulse is found to be as small about 5 mmHg which would make it difficult to distinguish the pulse from the normally expected artifacts.

Accordingly, it is a primary object of the present invention to provide an improved blood pressure measuring system capable of well distinguishing the blood pressure pulse from the artifacts and assuring accurate analysis of the pulses for reliable determination of the blood pressure measurements.

In the present invention there are disclosed some advantageous schemes of defining the pulsating quantity as the integral of the pulse in a more consistent way with the actual behavior of the blood pressure pulse train in an attempt to provide more reliable blood pressure measurements.

It is therefore another object of the present invention to provide an improved blood pressure measuring system enabling the consistent and accurate analysis of the blood pressure pulses for more reliable blood pressure measurements.

These and other objects of the present invention will be apparent from the following detailed description of the invention when taken in conjunction with the accompanying drawings.

DETAILED DESCRIPTION OF THE PREFERRED EMBODIMENT

Figure 1:
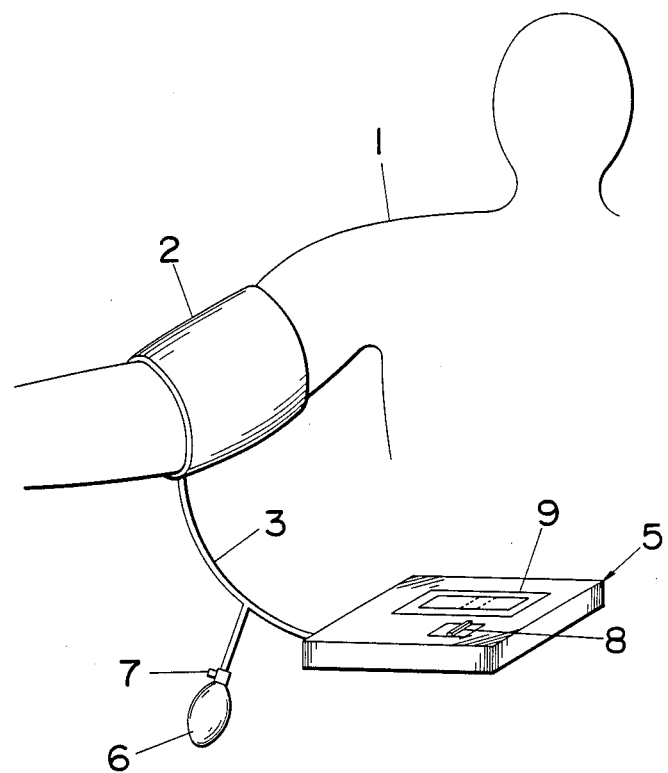
FIG. 1 is a schematic view of an apparatus embodying a blood pressure measuring system of the present invention, the apparatus being shown with its occluding cuff fitted around the upper arm of a test subject.

Referring now to FIG. 1, there is shown a blood pressure measuring system embodying the present invention. The system includes an occluding cuff 2 of conventional design to be fitted around the upper arm of a test subject 1 for occluding the artery therein. The occluding cuff 2 is connected by way of a tube 3 to a pressure transducer 4 mounted within an apparatus body 5 together with associated electronics. The apparatus body 5 is formed with a power switch 8 and a display 9 for indicating the results of the blood pressure measurements as decimal numbers. Connected to the tube 3 midway between the occluding cuff 2 and the pressure transducer 4 is an pump-up inflation bulb 6 with a bleed valve 7 for inflating the occluding cuff 2 and then allowing the occluding pressure to gradually decrease. It is within this gradually decreasing pressure period that the blood pressure measurements are effected based upon oscillometric methods.

Figure 2:
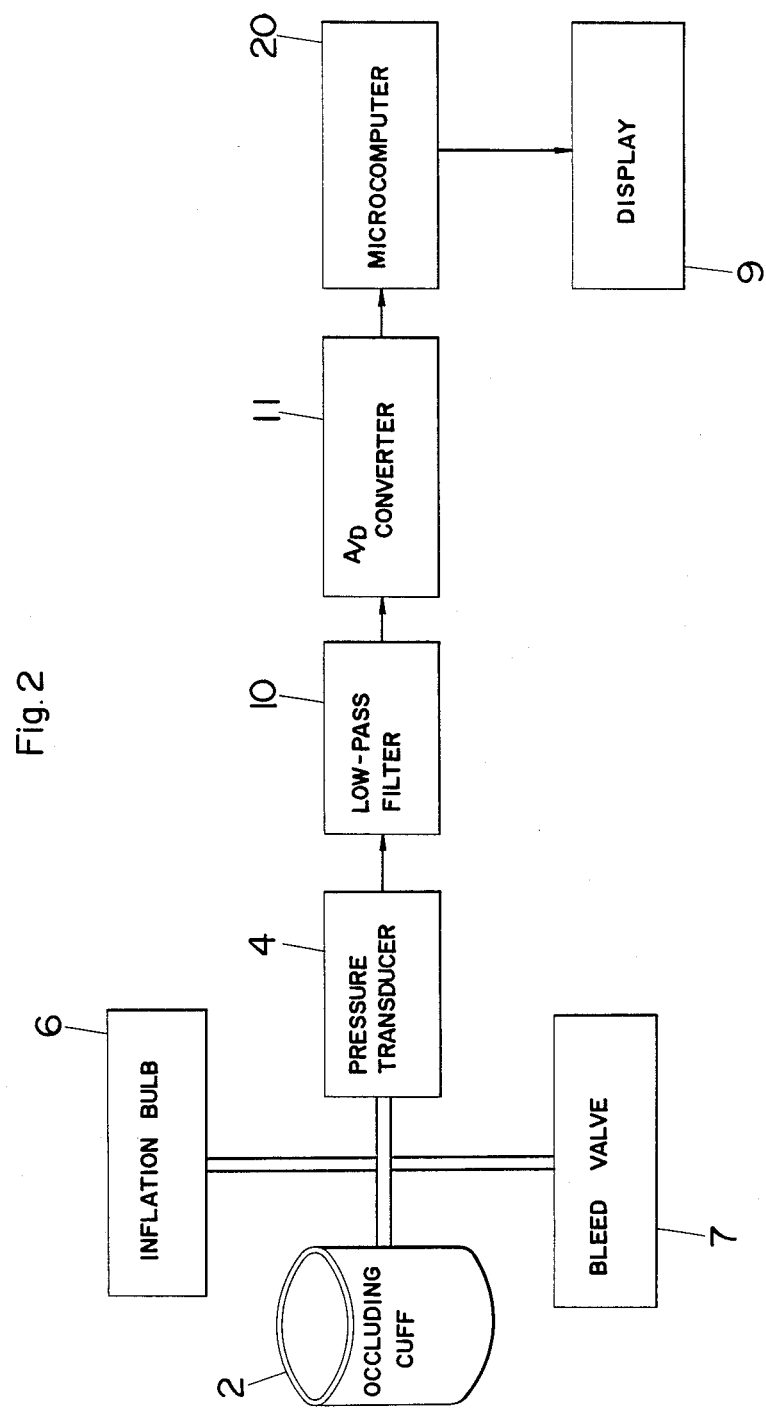
FIG. 2 is a block diagram of the above system.
Figure 4:
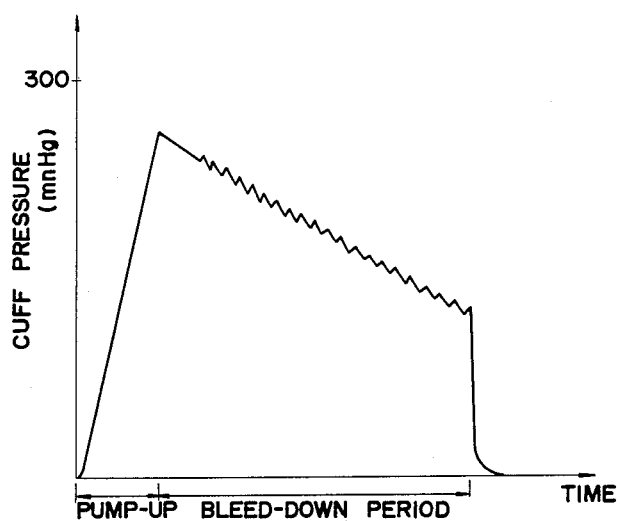
FIG. 4 is a waveform diagram showing the envelope of sampled cuff pressure plotted with respect to time within a measurement cycle of the above system.

As shown in FIG. 2, the electronics mounted within the apparatus body 5 includes, in addition to the pressure transducer 4, a low-pass filter 10, analog-digital converter 11, and a microcomputer 20 which processes the output from the pressure transducer 4 in a programmed manner for determination of the blood pressure measurements as well as for indication of the measured results on the display 9. The microcomputer 20 comprises a central processor unit (CPU) together with a program memory (ROM) and a data memory (RAM). The output of the pressure transducer 4 is continuously fed to the analog-digital converter 11 through the low-pass filter 10 having a cut-off frequency of about 10 to 20 Hz in order to suppress artifacts and noise signals which are in the lower frequency band outside of the signal band of interest and to only pass the signal of desired frequencies well representative of the sensed cuff pressure. At the analog-digital converter 11, the sensed cuff pressure, which is the sum of a static pressure applied to the occluding cuff 2 and an arterial blood pressure pulse induced in the time period of bleeding down the cuff pressure after completely occluding the artery, is sampled at a sufficiently higher rate of about 10 to 100 Hz to faithfully reproduce the sensed cuff pressure, as shown in FIG. 4. The sampled data are then fed to the microcomputer 20 which processes the data obtained during the time period of bleeding down the cuff pressure for determination of the systolic and diastolic pressures.

Figure 3:
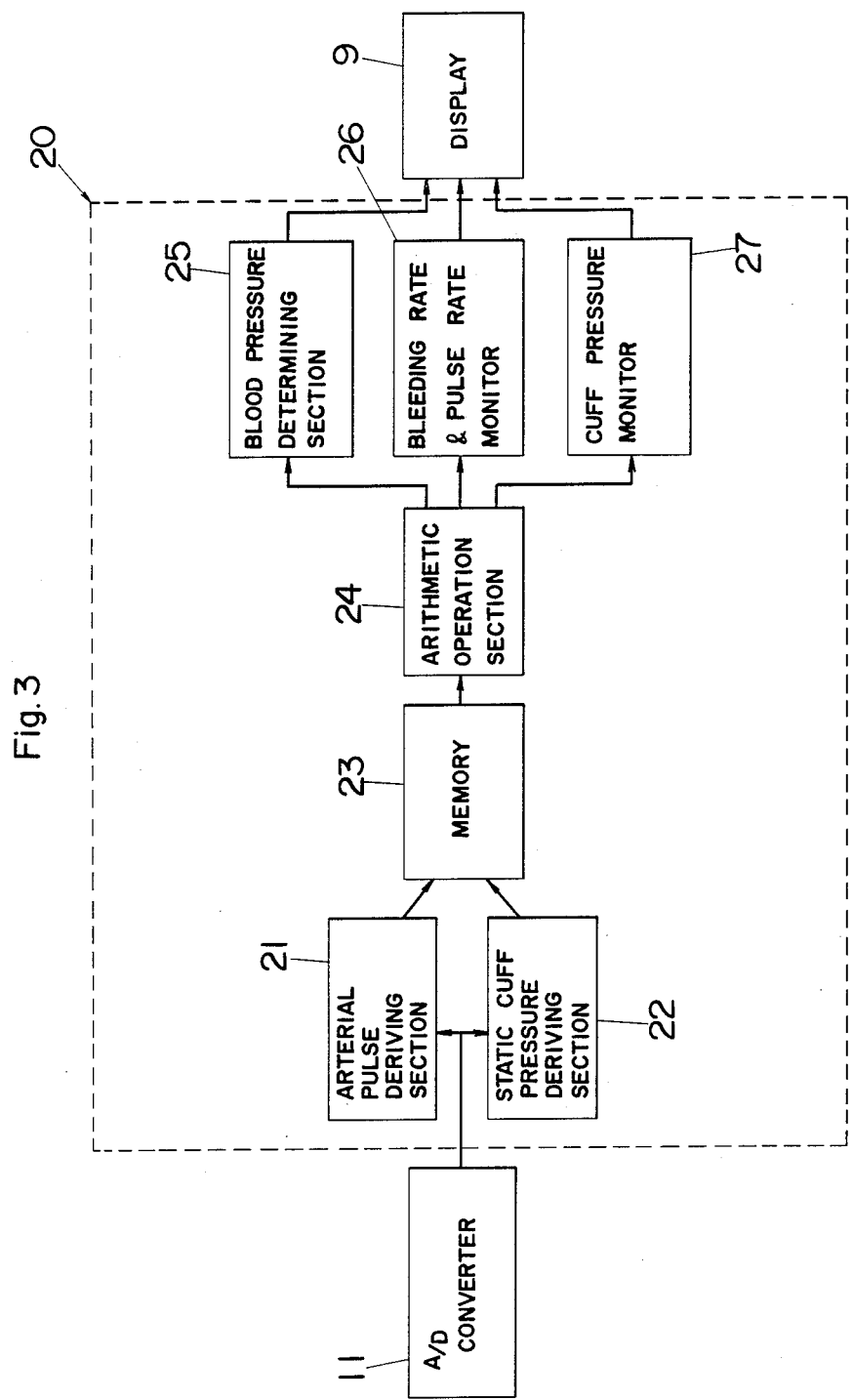
FIG. 3 is a block diagram showing the details of a portion of the above system.
Figure 7:
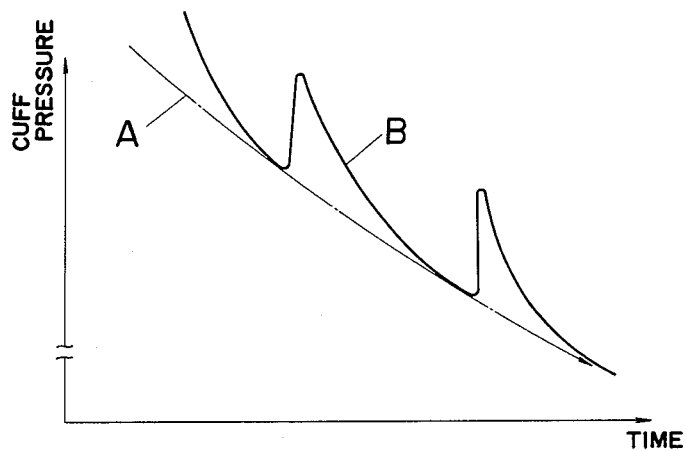
FIG. 7 is an enlarged view of a portion of FIG. 4.

Referring to FIG. 3, the microcomputer 20 constitutes an arterial pulse component deriving section 21, static cuff pressure deriving section 22, memory 23, arithmetic operation section 24, blood pressure determining section 25, bleeding rate and pulse rate monitor 26, cuff pressure monitor 27. The arterial pulse component deriving section 21 is for extracting from the sampled cuff pressure data a pulsating quantity representing each of the blood pressure pulses occurring in sequence. The static cuff pressure deriving section 22 is for extracting from the same sampled cuff pressure data the static cuff pressure which decreases gradually and smoothly during the bleeding period as schematically indicated by line A of FIG. 7, in which the sampled cuff pressure, i.e., the sum of the static pressure and the superimposed blood pressure pulse is indicated by a curve B.

Figure 8:
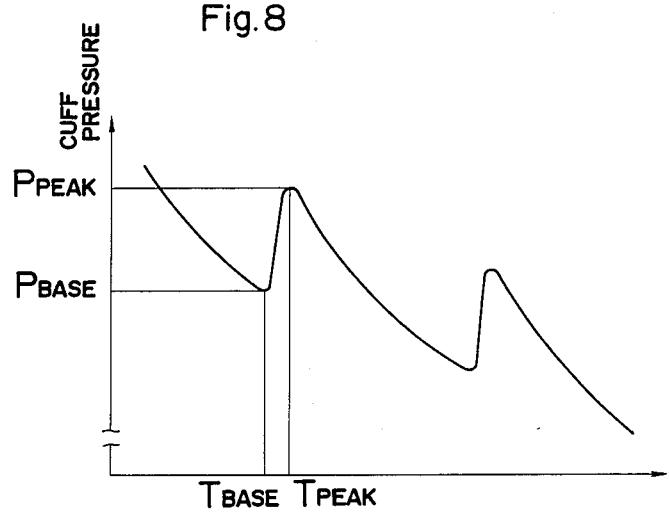
FIG. 8 is an explanatory view, similar to FIG. 7, showing on the envelope of the sampled cuff pressure respective points utilized for extraction of the pulsating quantity and the static cuff pressure.
Figure 9:
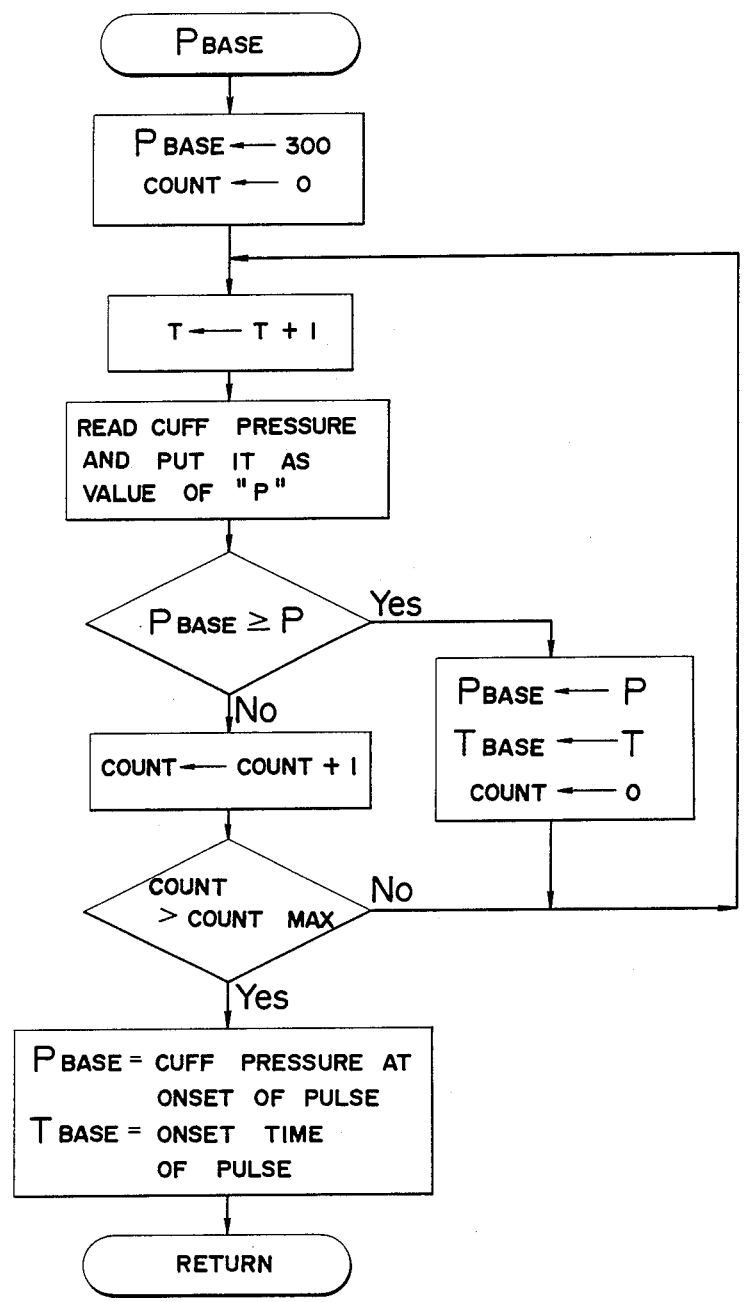
FIGS. 9 and 10 are flow charts respectively showing the procedures of obtaining the static cuff pressure at the onset of the blood pulse and the peak value of the sampled cuff pressure within the duration of the blood pressure pulse.
Figure 10:
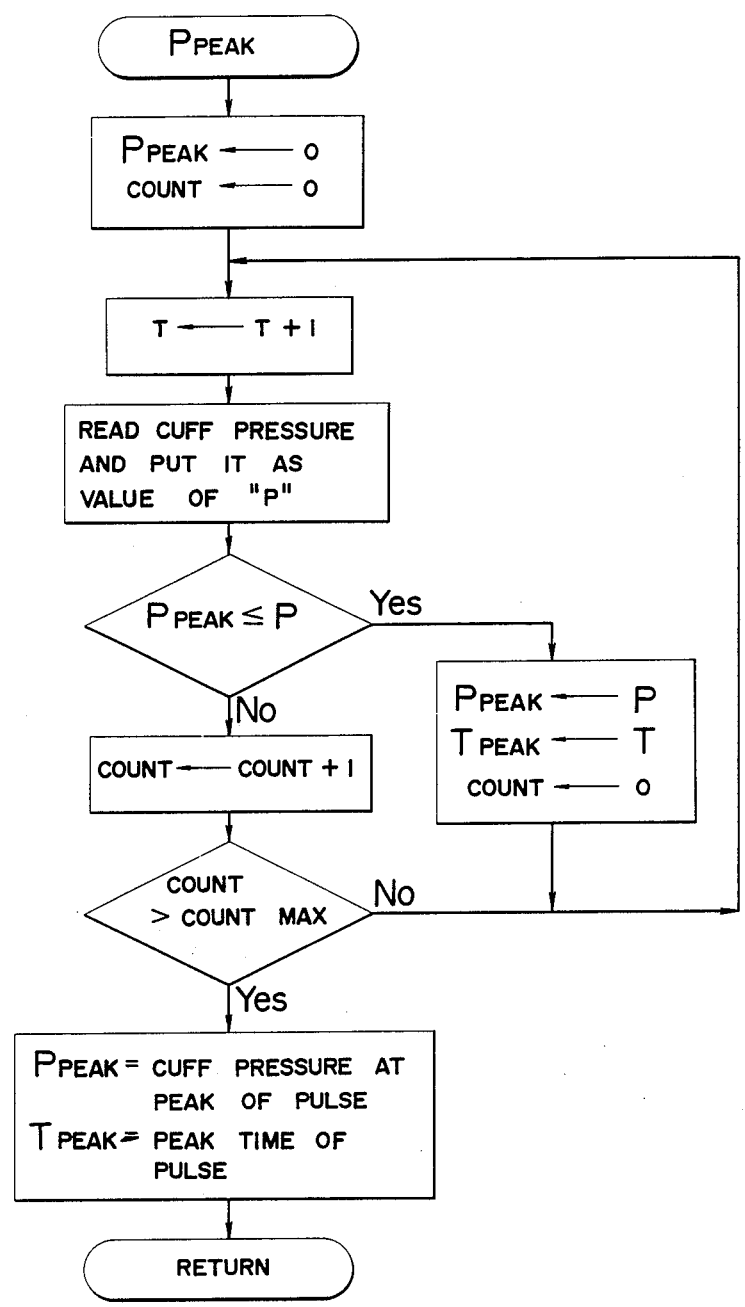

It should be noted at this time that the pulsating quantity is defined in terms of an integral of the blood pressure pulse superimposed upon the static cuff pressure and that the pulsating quantity and the static cuff pressure are calculated from some or all of the values at points on the envelope curve of the sampled cuff pressure data. These points are, as shown in FIG. 8, $P_{BASE}$ indicating the pressure level at the onset of the pulse, $T_{BASE}$ being the onset time of the pulse, $P_{PEAK}$ the pressure level at the peak of the pulse, and $T_{PEAK}$ being the peak time of the pulse, these values being obtained in accordance with operational sequences illustrated in FIGS. 9 and 10. The operational sequence of FIG. 9 concludes $P_{BASE}$ and $T_{BASE}$ on the assumption that the cuff pressure never be increased above 300 mmHg which is much higher even than the maximum systolic pressure expected for a hypertensive. That is, during the period of decreasing the cuff pressure after completely occluding the artery at a pressure below 300 mmHg, the "$P_{BASE}$" is continuously updated to be the decreasing cuff pressure sensed until the latter turns to increase due to the presence of the superimposed blood pressure pulse and such increase lasts over a certain time interval defined by "COUNT MAX". The value of "COUNT MAX" is selected to be large enough for neglecting an instantaneous increase of the pressure representative of mere artifacts or other noise signal other than the blood pressure pulse of interest. In this manner, the "$P_{BASE}$" which is the static cuff pressure at the onset of the blood pressure pulse is obtained together with "$T_{BASE}$", the onset time of the pulse. In the operational sequence of FIG. 10, on the other hand, the "$P_{PEAK}$" is continuously updated to be the increasing cuff pressure sensed until it turns to again decrease and such decrease last over a reasonable time interval defined by "COUNT MAX". Thus, the "$P_{PEAK}$" which is the cuff pressure at the peak of the pulse is obtained together with "$T_{PEAK}$", the peak time of that pulse.

Figure 11:
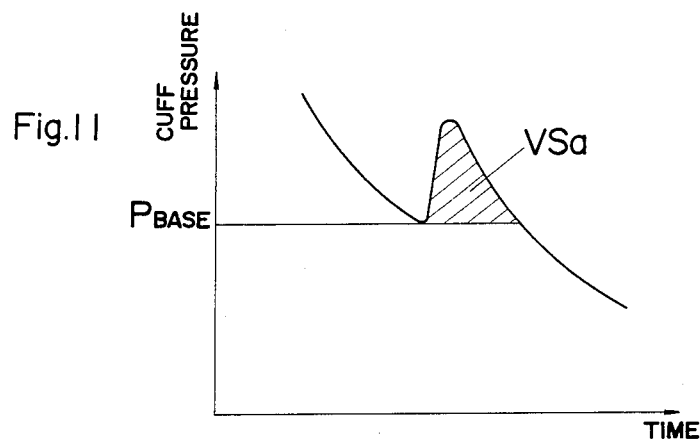
FIGS. 11 to 13 are explanatory views respectively showing different methods of obtaining the pulsating quantity as an integral of the blood pressure pulse.

In the present invention there are utilized several advantageous schemes of obtaining the pulsating quantity in terms of the integral of the blood pulse. One simplest scheme is, as shown in FIG. 11, to calculate the quantity as the area VSa of region bounded by the curve of the pulse above the value of "$P_{BASE}$" which is the cuff pressure at the onset of that pulse. The pulsating quantity thus obtained as the area VSa for each of the blood pressure pulses appearing in sequence during the measurement cycle is plotted with respect to time in FIG. 5 of which time axis is in exact coincidence with that of FIG. 4 showing the sampled cuff pressure and that of FIG. 6 showing the sequence of the static cuff pressures or the pressure levels at the onsets of the recurring pulses. These time-dependent values of the pulsating quantity VSa and the static cuff pressure are respectively stored in the memory 23 and are to be read out in the subsequent operation of determining the blood pressure measurements and monitoring the bleeding and pulse rate at the sections 24, 25 and 26. The section 24 also handles the on-the-fly data through the memory 23 in such a way that the cuff pressure monitor 27 responds to indicate on the display 9 the cuff pressure being sensed in the measurement cycle.

Figure 5:
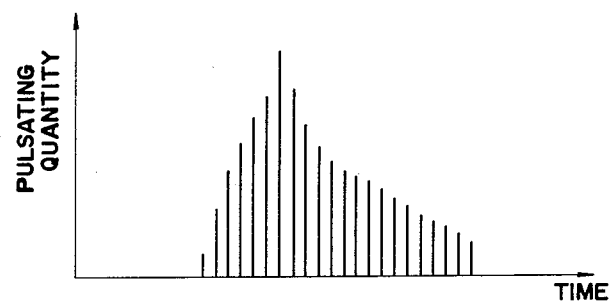
FIG. 5 is a diagram of the pulsating quantities with respect to time within the measurement cycle of the FIG. 4, the pulsating quantity being extracted from the sampled cuff pressure of FIG. 4.
Figure 6:
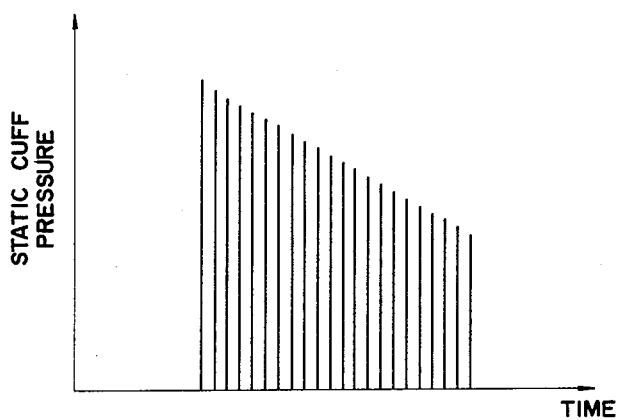
FIG. 6 is a diagram of static cuff pressures with respect to time within the measurement cycle of FIG. 4, the static cuff pressure being extracted from the sampled cuff pressure of FIG. 4.

As typically shown in FIG. 5, the train of the pulsating quantities shows the characteristic pattern of the blood pressure pulses appearing in the bleeding period of gradually decreasing the occluding pressure, which pattern gives a proper criterion for determining the systolic and diastolic pressures based upon the oscillometric methods. For this purpose, the train of the pulsating quantities is analyzed at the section 24 to provide the criterion which is then utilized in the section 25 for determination of the systolic and diastolic pressures, the details of which will be described hereinafter.

Figure 12:
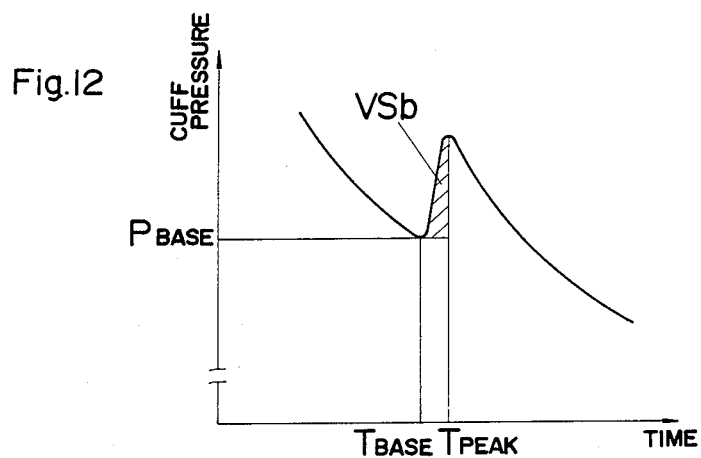

Referring to FIG. 12, another scheme of obtaining the pulsating quantity is shown in which the quantity is defined to be the area VSb of the region bounded by the pulse curve between the limits $T = "T_{BASE}"$ and $T = "T_{PEAK}"$ above the pressure level $P = "P_{BASE}"$. This is based upon the acknowledgment that the component of the integral of the pulse curve past the pulse peak will be likely to fluctuate depending upon the the bleeding rate of the cuff pressure and is preferred to be eliminated for providing an index faithfully representing the characteristic behavior of the blood pressure pulse. Consequently, the pulsating quantity thus obtained can well serve to ensure more consistent analysis of the blood pressure pulses, resulting in reliable determination of the blood pressure measurements.

Figure 13:
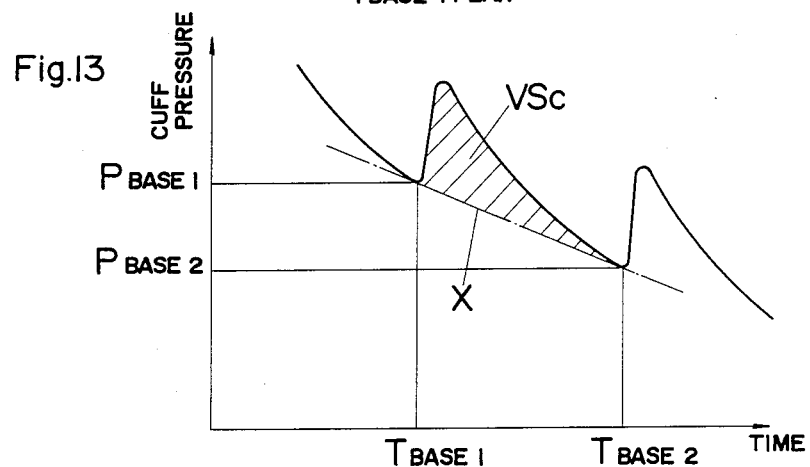

A further advantageous scheme of obtaining the pulsating quantity is shown in FIG. 13 in which the quantity is defined to be the area VSc of the region bounded by the pulse curve between the limits $T = "T_{BASE1}"$ and $T = "T_{BASE2}"$ above an approximate line X of descending cuff pressure passing through the coordinates ($T_{BASE1}, P_{BASE1}$) and ($T_{BASE2}, P_{BASE2}$), where "$P_{BASE2}$" is the cuff pressure at the onset of the subsequent blood pressure pulse and "$T_{BASE2}$" the onset time of that subsequent pulse. This scheme takes into account the fact that the static cuff pressure upon which the pulse is superimposed will be constantly decreasing as the blood pulse changes its amplitude, resulting in faithful representation of the true blood pressure pulse for effecting more reliable determination of the blood pressure measurements.

Figure 14:
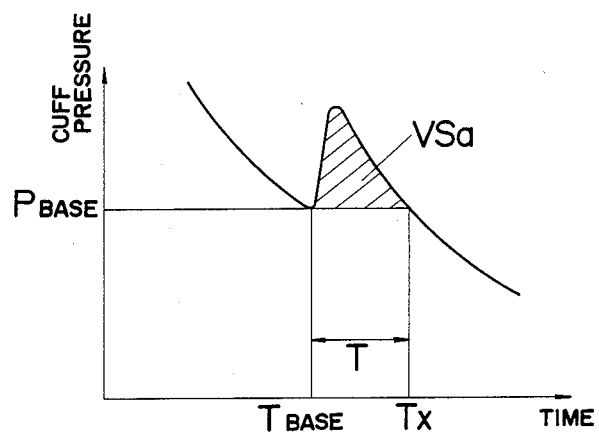
FIGS. 14 and 15 are explanatory views respectively showing other applicable method of obtaining the pulsating quantity in terms of the integral of the blood pressure pulse.

Besides the above, still other effective schemes can be utilized in the present invention which define the pulsating quantity to be the quotient of an integral of the blood pressure pulse by a particular value of time within the time period of the blood pressure, i.e., to be the mean pressure level obtained by dividing the integral of the pulse by the particular value of time. FIG. 14 shows one of the above schemes which handles the pulsating quantity as the mean pressure value VSa/T, where VSa is the area of region defined in the scheme of FIG. 11 and T is a time interval from the onset time "$T_{BASE}$" of the pulse to the instant "Tx" when the cuff pressure decreases down to the same level "$P_{BASE}$" at the onset of the pulse. With this scheme of obtaining the mean pressure of the pulse, it is possible to compensate for any distortion of the pulse waveform due to the existence of artifacts or other noises induced such as by the motion of the subject or other unknown reason, which distortion would unduly elongate the value T or pulse width and therefore provide unreliable area VSa of region. Accordingly, the present scheme can successfully eliminate such artifacts or noises unduly distorting the blood pressure pulse, contributing to a reliable determination of the blood pressure measurements.

Figure 16:
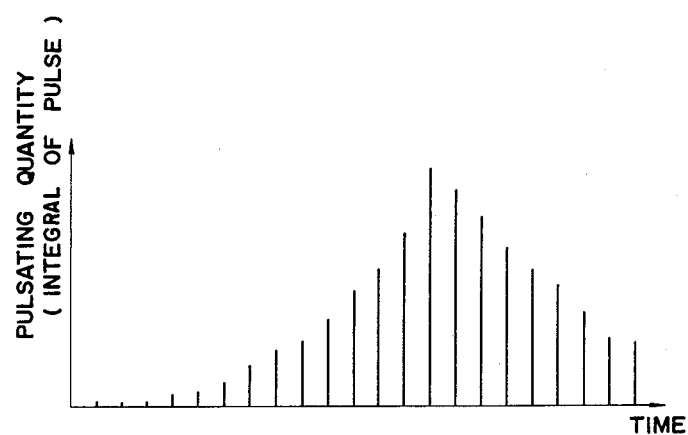
FIG. 16 is a diagram showing a train of the pulsating quantities obtained by the method of FIG. 11.
Figure 17:
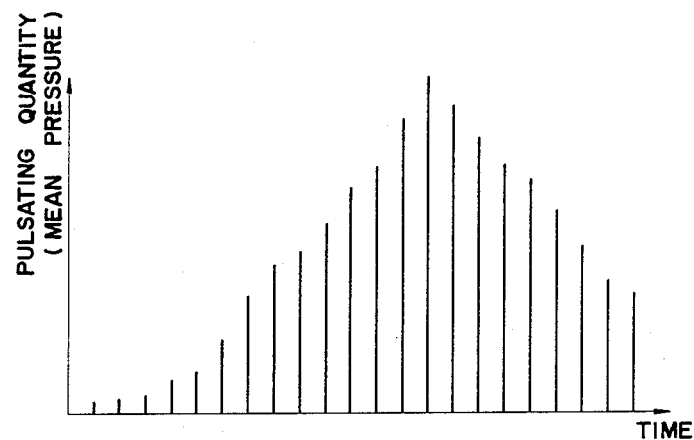
FIG. 17 is a diagram showing a train of the pulsating quantities obtained by the method of FIG. 15.

As shown in FIG. 17, the train of the pulsating quantity obtained in accordance with the above scheme indicates the like tendency or characteristic pattern as seen in FIG. 16 which shows the train of the pulsating quantity in accordance with the scheme of FIG. 11, and is acknowledged to be an effective alternative thereof while retaining the above advantageous feature of effectively eliminating the artifacts or noise.

Figure 15:
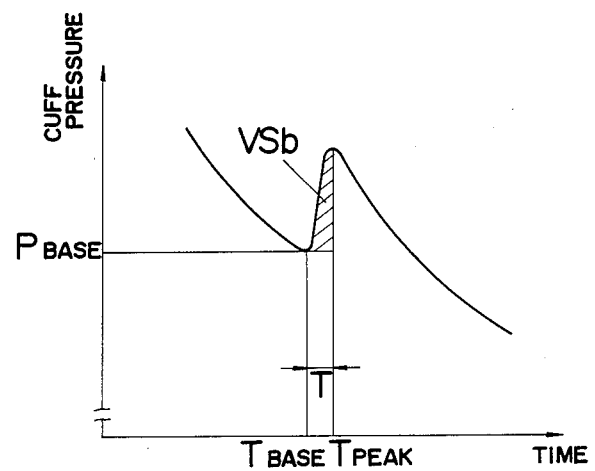

FIG. 15 illustrates another effective scheme for obtaining the pulsating quantity as the mean pressure level of the blood pressure pulse. In this scheme, the mean pressure level is calculated by dividing the area of region VSb measured in the manner shown in FIG. 12 by the time period $T = "T_{PEAK}" - "T_{BASE}"$. Accordingly, the present scheme enjoys the advantage of eliminating the useless component which will fluctuate with varying bleeding rate as described hereinbefore with reference to FIG. 12 in addition to the advantages of eliminating the artifacts or noises as described in the above with reference to FIG. 14.

Figure 18:
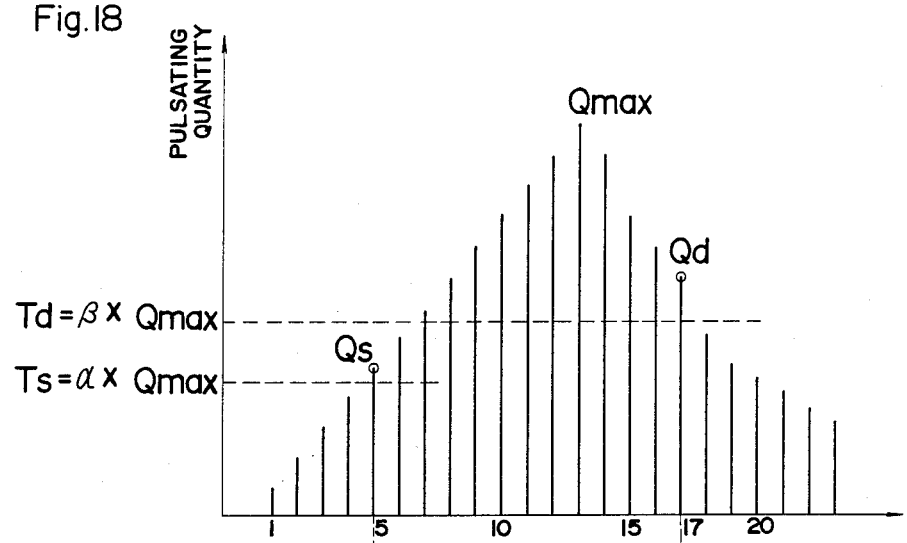
FIGS. 18 and 19 are diagrams which are cooperative to explain criteria for determination of systolic and diastolic pressures utilizing the individual trains of pulsating quantities and the static cuff pressures.
Figure 19:
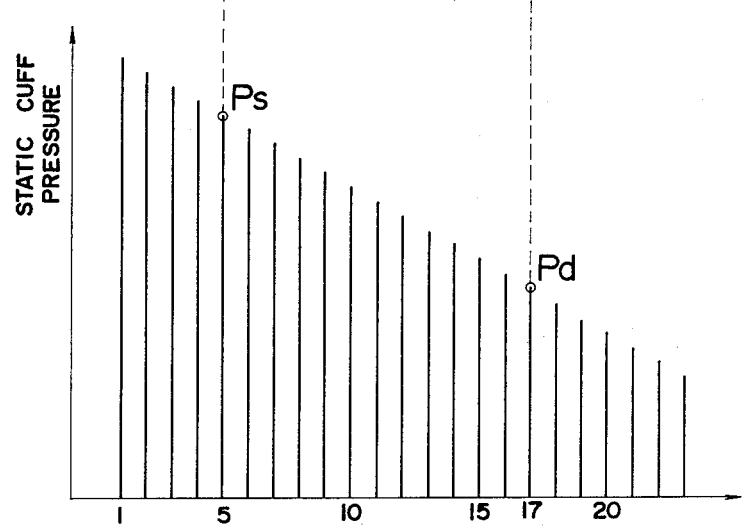

Referring now to FIGS. 18 and 19, there is illustrated one analytical method of determining the systolic and diastolic pressures based upon the pulsating quantity obtained in accordance with the present invention. The pulsating quantity for each of the blood pressure pulses appearing in the bleeding period of decreasing the cuff pressure is registered in the memory 23 and is read out for processing at the arithmetic operation section 24 after all the quantities have been measured. The section 24 calculates based upon the pulsating quantities in the memory 23 a set of thresholds, one for determination of the systolic pressure and the other for the diastolic pressure. These threshold are determined each to be the function of the maximum pulsating value "Qmax", which corresponds to the value of the 13th occurrence in the pulsating quantity train of FIG. 18. The thresholds Ts and Td for the systolic and diastolic pressures are defined in the present invention to be individual fractions of "Qmax", as expressed in the following expressions $Ts = \alpha \times Qmax$, and $TRd = \beta \times Qmax$, where $0 < \alpha, \beta < 1$. It is the operation of the section 24 that calculates these thresholds Ts and Td fromt he maximum pulsating quantity "Qmax". Following this calculation, the blood pressure determining section 25 is in operation to find the first pulsating quantity Qs that exceeds the systolic threshold Ts and the last pulsating quantity Qd just before falling down through the diastolic threshold Td, the former value corresponding to the 5th occurrence and the latter value to the 17th occurrence in the train of the pulsating quantities of FIG. 18. The first advent of the pulsating quantity Qs above the "Ts" is utilized as an index of the systolic pressure and the last advent of the pulsating quantity Qd above the "Td" as the diastolic pressure. In this way, the section 25 determines which pulsating quantity corresponds to each of the systolic and diastolic pressures and reads out from the memory 23 the value of the static cuff pressure corresponding to the particular pulsating quantity indicating the advent of each of the systolic and diastolic pressures, the values thus determined being displayed on the display 9. That is, in the illustrated example of FIG. 19, the systolic and diastolic pressure are respectively determined to be the values of the static cuff pressures in the 5th and 17th occurrences in the decreasing train of the static cuff pressures.

Figures 20, 21:
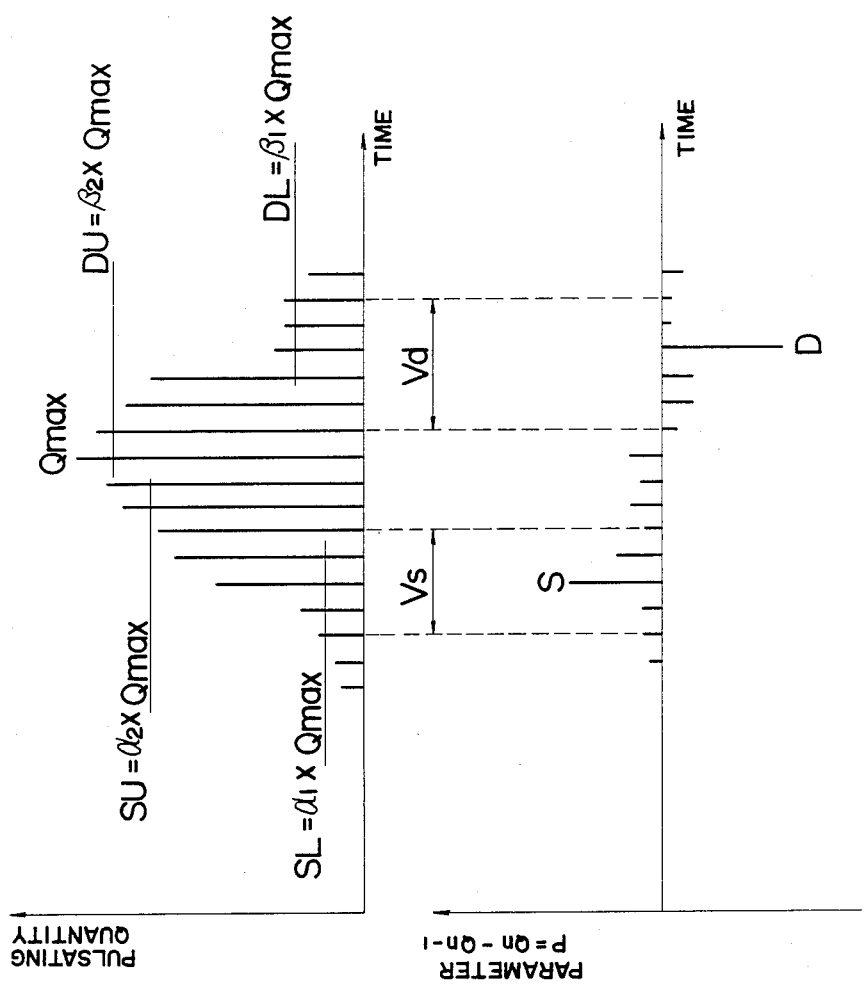
FIGS. 20 and 21 are diagrams which are cooperative to explain another criteria for determination of systolic and diastolic pressures utilizing the individual trains of the pulsating quantities and the parameter obtained therefrom.

Another analytical method of determinating the systolic and diastolic pressures will be discussed with reference to FIGS. 20 and 21. In this method, there is introduced a parameter for determination as to which pulsating quantity corresponds the systolic and diastolic pressures. The parameter P is the difference between the values of the two adjacent pulsating quantities as expressed in the equation $P=Qn-Q_{n-1}$, where Qn is the value of the pulsating quantity in the n-th occurrence.

The systolic and diastolic pressures are determined by examining the values of the parameters such that a maximum parameter indicated by S in the figure corresponds to the systolic pressure and that a minimum parameter indicated by D in the figure corresponds to the diastolic pressure. For effecting a reliable determination less susceptible to artifacts, the present method includes validation periods Vs and Vd for the respective determination of the systolic and diastolic pressures, each defining the valid period only within which the pulsating quantity representative of the systolic or diastolic pressure is expected to appear. Thus, the system can present a reliable measurement as eliminating the artifacts appearing outside of the validation periods and having the value which would otherwise be determined to be representative of the systolic or diastolic pressure and accordingly would lead to false determination. These validation periods Vs and Vd are defined respectively in terms of the maximum pulsating quantity "Qmax", i.e., the validation period Vs corresponds to the time interval during which the pulsating quantities fall between the lower limit $SL=\alpha_1 \times Qmax$ and the upper limit $SU=\alpha_2 \times Qmax$, while the validation period Vd corresponds to the time interval during which the pulsating quantities fall between the lower limit $DL=B1 \times Qmax$ and the upper limit $DU=\beta_2 \times Qmax$, where $0<\alpha_1, \alpha_2, \beta_1, \beta_2<1$, and $\alpha_1<\alpha_2, \beta_1<\beta_2$.

It is noted at this time that there could be employed other analytical methods of determining the systolic and diastolic pressures based upon the pulsating quantity obtained in accordance with the present invention. However, it is found that most consistent, reliable and economical blood pressure measurements can be achieved when the systolic pressure is determined in the manner shown in FIGS. 18 and 19 and at the same time the diastolic pressure is determined in the manner shown in FIGS. 20 and 21.

What is claimed is:

1. A blood pressure measuring system comprising:
   an occluding cuff attachable to a test subject for applying a varying occluding pressure thereto in the vicinity of an artery;
   pressure bleeding means for gradually decreasing the occluding pressure;
   pressure transducer means communicating with said occluding cuff for producing an instantaneous cuff pressure measurement which is the sum of an instantaneous static cuff pressure plus an instantaneous pulsating blood pressure indicative of each blood pressure pulse superimposed on said static cuff pressure;
   an analog-digital converter coupled to the pressure transducer means for sampling and converting said instantaneous cuff pressure measurement at a suitable sampling rate substantially more frequent than a rate of said blood pressure pulses into corresponding cuff pressure data in digital form, said cuff pressure data being monitored during the course of decreasing the occluding pressure from a point of substantially occluding the artery to a point of substantially unoccluding the artery so that said cuff pressure data are obtained from said instantaneous cuff pressure measuraement including said instantaneous pulsating blood pressure superimposed thereon and showing a generally decreasing relationship with respect to elapsed time;
   static cuff pressure deriving means for extracting from said sampled cuff pressure digital data instantaneous static cuff pressures corresponding to the onset of each blood pressure pulse during the course of decreasing the occluding pressure;
   arterial pulse component deriving means for extracting from said sample cuff pressure digital data a pulsating quantity representing the intensity of each of said blood pressure pulses appearing in sequence during the courase of decreasing the occluding pressure, said arterial pulse component deriving means operating to integrate values of sampled cuff pressure data for each blood pressure pulse above an offset value corresponding to the instantaneous static cuff pressure at the onset of the pulse over a time period of a portion of the blood pressure pulse so that said pulsating quantity is derived in terms of an integral of each blood pressure pulse above said offset pressure valaue corresponding to the static blood pressure at onset of the associated blood pressure pulse, for a time period starting from the onset of said blood pressure pulse to at least the peak of said blood pressure pulse;
   memory means for storing said pulsating quantitites and said sampled values of static cuff pressures associated with each pulsating quantity;
   blood pressure determining means which analyzes changes in the successive train of said pulsating quantities and said sampled values so as to determine values of systolic and diastolic pressures which are, respectively, static cuff pressures corresponding to each of said changes in said pulsating quantities; and
   display means for displaying the respective values of systolic and diastolic pressures.

2. A blood pressure measuring system as set forth in claim 1, wherein said pulsating quantity is derived as an integral of the entire blood pressure pulse above said offset pressure value.

3. A blood pressure measuring system as set forth in claim 1, wherein said pulsating quantity is derived as an integral of said blood pressure pulse above said offset pressure value for a time period starting from the onset of said blood pressure pulse to the peak of said blood pressure pulse.

4. A blood pressure measuring system as set forth in claim 1, wherein said pulsating quantity is derived as the quotient of an integral of said entire blood pressure pulse above said offset pressure value divided by a limited time interval, said integral of said entire blood pressure pulse being calculated for a time period starting from the onset of said blood pressure pulse to a point at which said blood pressure pulse decreases to the level of said offset pressure value, and said limited time interval corresponding to said time period.

5. A blood pressure measuring system as set forth in claim 1, wherein said pulsating quantity is derived as the quotient of an integral of said blood pressure pulse above said offset pressure value divided by a limited time interval, said integral of said blood pressure pulse being calculated for a time period starting from the onset of said blood pressure pulse to the peak thereof, and said limited time interval corresponding to said time period.

* * * * *